US009914918B2

(12) United States Patent
Margaritis et al.

(10) Patent No.: US 9,914,918 B2
(45) Date of Patent: Mar. 13, 2018

(54) FVII POLYPEPTIDE VARIANTS EXHIBITING ALTERED INTERACTION WITH ENDOTHELIAL PROTEIN C RECEPTOR (EPCR) AND METHODS OF USE THEREOF FOR MODULATING HEMOSTASIS

(71) Applicant: The Children's Hospital of Philadelphia, Philadelphia, PA (US)

(72) Inventors: Paris Margaritis, Ardmore, PA (US); Giulia Pavani, Voghenza (IT)

(73) Assignee: The Children's Hospital of Philadelphia, Philadelphia, PA (US)

( * ) Notice: Subject to any disclaimer, the term of this patent is extended or adjusted under 35 U.S.C. 154(b) by 88 days.

(21) Appl. No.: 14/553,677

(22) Filed: Nov. 25, 2014

(65) Prior Publication Data

US 2015/0210994 A1 Jul. 30, 2015

Related U.S. Application Data

(63) Continuation-in-part of application No. PCT/US2013/042829, filed on May 28, 2013.

(60) Provisional application No. 61/651,949, filed on May 25, 2012, provisional application No. 61/731,790, filed on Nov. 30, 2012, provisional application No. 61/790,098, filed on Mar. 15, 2013.

(51) Int. Cl.

| | |
|---|---|
| ***C12N 9/64*** | (2006.01) |
| ***A61K 9/127*** | (2006.01) |
| ***A61K 38/36*** | (2006.01) |
| ***A61K 38/48*** | (2006.01) |

(52) U.S. Cl.
CPC ............ *C12N 9/6437* (2013.01); *A61K 9/127* (2013.01); *A61K 38/36* (2013.01); *A61K 38/4846* (2013.01); *C12Y 304/21021* (2013.01)

(58) Field of Classification Search
None
See application file for complete search history.

(56) References Cited

U.S. PATENT DOCUMENTS

2010/0166729 A9* 7/2010 Madison .............. C07K 14/745 424/94.64
2010/0260741 A1* 10/2010 Haaning .............. C12N 9/6437 424/94.64

OTHER PUBLICATIONS

Disse, J., et al. 2011 The Journal of Biological Chemistry 286(7): 5756-5767.*
Preston et al., Multifunctional specificity of the protein C/activated protein C Gla domain, J Biol Chem., 2006, 28850-7, 281.
Ghosh et al., Endothelial cell protein C receptor acts as a cellular receptor for factor VIIa on endothelium, J Biol Chem., 2007, 11849-57, 282.
Hoffman et al., Tissue factor around dermal vessels has bound factor VII in the absence of injury, J Thromb Haemost., 2007, 1403-8, 5.
Konkle et al., Randomized, prospective clinical trial of recombinant factor VIIa for secondary prophylaxis in hemophilia patients with inhibitors, J Thromb Haemost., 2007, 1904-13, 5.

* cited by examiner

*Primary Examiner* — Marsha Tsay
(74) *Attorney, Agent, or Firm* — Kathleen D. Rigaut; Dann, Dorfman, Herrell & Skillman

(57) ABSTRACT

Factor VII variants and methods of use thereof are disclosed.

15 Claims, 15 Drawing Sheets

FIGURE 6

Mature Human FVIIa protein sequence (start of Gla domain): ANAFLEELR P
1 2 3 4 5 6 7 8 9 1 0

| Variant # | Amino acid replacing Phe4 | Variant # | Amino acid replacing Leu8 |
|---|---|---|---|
| 1 | W | 19 | W |
| 2 | G | 20 | G |
| 3 | E | 21 | F |
| 4 | D | 22 | S |
| 5 | V | 23 | Y |
| 6 | K | 24 | P |
| 7 | F | 25 | H |
| 8 | S | 26 | Q |
| 9 | Y | 27 | R |
| 10 | C | 28 | M |
| 11 | L | 29 | I |
| 12 | H | 30 | T |
| 13 | Q | 31 | A |
| 14 | R | 32 | V |
| 15 | M | | |
| 16 | I | | |
| 17 | T | | |
| 18 | N | | |

FIGURE 13

Mature Human FVII protein sequence (start of Gla domain): ANAFLEELR P
1 2 3 4 5 6 7 8 9 10

| Variant # | Amino acid replacing Phe4 |
|---|---|
| 1 | W |
| 2 | G |
| 3 | E |
| 4 | D |
| 5 | V |
| 6 | K |
| 7 | F |
| 8 | S |
| 9 | Y |
| 10 | C |
| 11 | L |
| 12 | H |
| 13 | Q |
| 14 | R |
| 15 | M |
| 16 | I |
| 17 | T |
| 18 | N |

| Variant # | Amino acid replacing Leu8 |
|---|---|
| 19 | W |
| 20 | G |
| 21 | F |
| 22 | S |
| 23 | Y |
| 24 | P |
| 25 | H |
| 26 | Q |
| 27 | R |
| 28 | M |
| 29 | I |
| 30 | T |
| 31 | A |
| 32 | V |

FVII POLYPEPTIDE VARIANTS EXHIBITING ALTERED INTERACTION WITH ENDOTHELIAL PROTEIN C RECEPTOR (EPCR) AND METHODS OF USE THEREOF FOR MODULATING HEMOSTASIS

This application is a continuation-in-part of PCT/US2013/042829, filed May 28, 2013, which claims priority to U.S. Provisional Application Nos. 61/651,949, 61/731,790, and 61/790,098 filed May 25, 2012, Nov. 30, 2012, and Mar. 15, 2013 respectively, the entire contents being incorporated herein by reference as though set forth in full.

FIELD OF THE INVENTION

The present invention relates to the fields of medicine and hematology. More specifically, the invention provides novel Factor VII polypeptide variants useful for the treatment of coagulation disorders.

BACKGROUND OF THE INVENTION

Several publications and patent documents are cited throughout the specification in order to describe the state of the art to which this invention pertains. Each of these citations is incorporated herein by reference as though set forth in full.

The current treatment of hemophilia is burdened by the development of antibodies to the factor infused in the patients to treat bleeding episodes. As a bypass to this complication, one successful mode of treatment includes infusion of recombinant activated FVII (rFVIIa) that can bring about cessation of bleeding even in the presence of such inhibitory antibodies. Unfortunately, rFVIIa has a very short circulating time in humans (~3 h) and therefore multiple injections need to be made in order to stop the bleeding. This escalates the cost of treatment tremendously and therefore development of alternative treatment strategies (either via improved proteins or gene-based therapies) is urgently needed.

SUMMARY OF THE INVENTION

In accordance with the present invention, we demonstrated that the endothelial protein C receptor (EPCR) plays a role in the hemostatic action of rFVIIa. As such, novel recombinant FVII polypeptide variants having enhanced EPCR binding capacity should demonstrate improved therapeutic activity when compared to the use of native FVIIa in methods for treatment of inherited coagulation disorders where recombinant activated FVII is typically used. Such disorders include, without limitation, hemophilia, FVII deficiency and platelet defects. Such variants include at least those shown in FIG. 6 (for human activated FVII) and FIG. 13 (for human FVII). Certain variants comprise 1, 2, 3 or 4 amino acid substitutions. In preferred embodiments, only one or two amino acids are substituted. Additionally, rFVIIa can persist well-beyond its circulatory half-life in extravascular space and EPCR appears to facilitate this. Such “idling” rFVIIa may form a complex with tissue factor and prevent bleeds in the microcirculation before they escalate to major bleeds. This may explain the clinical benefits of FVIIa-mediated long-term prophylaxis, Therefore, in the same range of clinical conditions, molecules that have enhanced EPCR binding capacities should be beneficial for long-term prophylaxis as well as during on-demand administration in response to bleeds. In addition, since EPCR binding of rFVIIa appears to sequester it from circulation as shown in FIG. 5, reducing EPCR binding should give rise to variant FVII polypeptides with increased circulatory half-lives which exhibit beneficial hemostatic effects that are observed for longer periods of time following treatment. Modifications that result in such effects are shown in FIG. 12 (for human activated FVII) and FIG. 13 (for human FVII). Thus, improvement of the net hemostatic outcome from treatment (prophylaxis or on-demand) can be achieved via administration of variant FVII polypeptides with enhanced EPCR binding (but shorter half lives) or from FVII polypeptides with reduced EPCR binding (but longer half-lives).

Thus, in accordance with the present invention, Factor VII variant polypeptides which exhibit modified pharmacokinetics and enhanced hemostatic capacity are provided. In a preferred embodiment, the variant FVII is a human variant, which exhibits altered endothelial protein C receptor binding relative to wild type human FVII. Also provided are nucleic acids encoding the variants described herein. Such nucleic acids are optionally cloned into an expression vector. Host cells comprising such expression vectors are also encompassed by the present invention.

In yet another aspect, a pharmaceutical composition comprising at least one of the Factor VII polypeptide variants described above in a biologically compatible carrier is provided.

The invention also provides a method for treatment of a hemostasis related disorder in a patient in need thereof, comprising administration of a therapeutically effective amount of the variant FVII described herein in a biologically acceptable carrier.

BRIEF DESCRIPTION OF THE DRAWINGS

FIG. 6. The amino acid sequence of the beginning of the Gla domain in the mature polypetide of human activated FVII is shown (SEQ ID NO: 10) along with the numbering of each amino acid position. The amino acids at position 4 and 8 are indicated with a red box. Variants of human activated FVII with modifications at these two positions are also shown.

FIG. 13. The amino acid sequence of the beginning of the Gla domain in the mature polypeptide of the wild-type human FVII is shown (SEQ ID NO: 10) along with the numbering of each amino acid position. The amino acids at position 4 and 8 are indicated with a red box. Variants of human FVII polypeptides with modifications at these two positions are also shown.

DETAILED DESCRIPTION OF THE INVENTION

Figure 1:
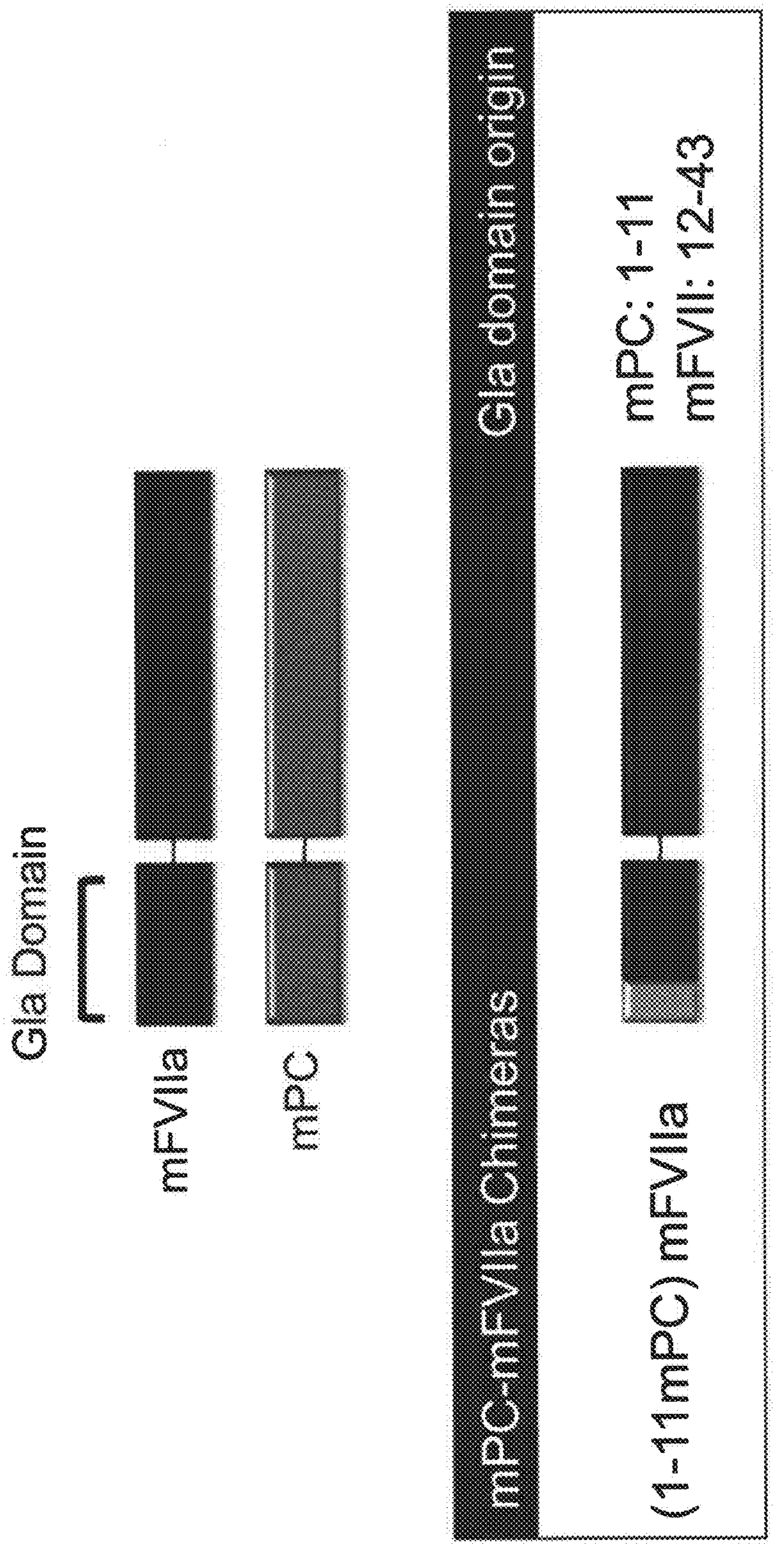
FIG. 1. Chimeric mouse FVIIa (mFVIIa) molecule was made by partial substitution of its Gla domains with that of mouse protein C (mPC).

The mode of action of high dose recombinant human FVIIa is not well understood but it involves multiple cellular as well as protein components of the coagulation system. Under therapeutic protein administration, FVIIa can directly activate coagulation factor X (generating Factor Xa), resulting in thrombin generation and clot formation. FVIIa's natural cofactor is tissue factor (TF), that when exposed to the circulation following injury, localizes the FVIIa coagulant reactions. However, the contribution of this pathway in hemophilia following FVIIa treatment is not entirely delineated. On the other hand, apart from effecting hemostasis, FVIIa has also been shown to interact with a cellular receptor (endothelial protein C receptor, EPCR) on the surface of endothelial cells that line blood vessels. Normally, this receptor for protein C is utilized to boost the anticoagulant pathway that controls excessive coagulation. Given data presented in this invention, it appears that under pharmacological administration, FVIIa binding to EPCR, enhances the hemostatic effects of FVIIa. Therefore, generation of FVII polypeptides that further enhance EPCR binding should give rise to molecules with an increased hemostatic capacity. At the same time, binding of FVIIa to EPCR reduces its circulatory half-life as shown in FIG. 5B. Therefore, generation of FVII variant polypeptides with reduced capacity to bind EPCR should also increase circulatory half-lives thereby providing increased hemostatic capacity due to prolongation of presence in the circulation.

Various terms relating to the biological molecules of the present invention are used hereinabove and also throughout the specification and claims.

The phrase "variant Factor VII polypeptide" refers to a modified FVII polypeptide which has been genetically altered such that the encoded protein exhibits altered binding for EPCR when compared to unmodified wild type FVII or wild type activated FVII. The nucleotide sequences described herein are readily obtainable from GenBank.

The phrase "hemostasis related disorder" refers to bleeding disorders such as hemophilia A, hemophilia A patients with inhibitory antibodies, hemophilia B, hemophilia B patients with inhibitory antibodies, deficiencies in coagulation Factors, VII, VIII, IX and X, XI, V, XII, II, von Willebrand factor, combined FV/FVIII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzmann thromblasthemia, and storage pool deficiency.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wisconsin. For convenience, the default parameters (gap creation penalty=12, gap extension penalty=4) specified by that program are intended for use herein to compare sequence identity. Alternately, the Blastn 2.0 program provided by the National Center for Biotechnology Information(found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. Preparation of Variant FVII Encoding Nucleic Acid Molecules and Polypeptides A. Nucleic Acid Molecules Nucleic acid molecules encoding the variant FVII polypeptides of the invention may be prepared by using recombinant DNA technology methods. The availability of nucleotide sequence information enables preparation of isolated nucleic acid molecules of the invention by a variety of means. For example, nucleic acid sequences encoding a variant FVII polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects coagulation function, it is preferable to express the molecule in mammalian cells.

Variant FVII-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting variant FVII expression.

B. Proteins

A variant FVII polypeptide of the present invention may be prepared in a variety of ways, according to known methods. The protein may be purified from appropriate sources, e.g., transformed bacterial or animal cultured cells or tissues which express engineered FVII by immunoaffinity purification.

The availability of nucleic acid molecules encoding a variant FVII polypeptide enables production of the variant FVII polypeptide using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of variant FVII protein may be produced by expression in a suitable prokaryotic or eukaryotic expression system. For example, part or all of a DNA molecule encoding variant Factor VII for example, may be inserted into a plasmid vector adapted for expression in a bacterial cell, such as *E. coli* or a mammalian cell such as CHO or Hela cells. Alternatively, in a preferred embodiment, tagged fusion proteins comprising FVII variant polypeptides can be generated. Such FVII-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant FVII proteins, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

Variant FVII proteins, prepared by the aforementioned methods, may be analyzed according to standard procedures. For example, such proteins may be assessed for altered coagulation properties according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may be conveniently achieved by culturing a host cell containing such a vector under appropriate conditions that cause or allow production of the polypeptide. Polypeptides may also be produced in in vitro systems.

III. Uses of variant FVII polypeptides and FVII-Encoding Nucleic Acids

Variant FVII nucleic acids encoding polypeptides having altered coagulation activities may be used according to this invention, for example, as therapeutic and/or prophylactic agents (protein or nucleic acid) which modulate the blood coagulation cascade or as a transgene in gene-, and or cell-based strategies for continuous expression of FVII polypeptide and its variants in patients with a hemostasis related disorders. The present inventors have discovered modifications of FVII molecules which result in altered pharmacokinetics and exhibit altered hemostatic properties.

A. Variant FVII Polypeptides

In a preferred embodiment of the present invention, variant FVII polypeptides may be administered to a patient via infusion in a biologically compatible carrier, preferably via intravenous injection. The variant FVII of the invention may optionally be encapsulated into liposomes or mixed with other phospholipids or micelles to increase stability of the molecule. Variant FVII polypeptides may be administered alone or in combination with other agents known to modulate hemostasis (e.g., Factor V, Factor Va, FVIII or derivatives thereof). An appropriate composition in which to deliver variant FVII polypeptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified variant FVII polypeptide contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the variant FVII polypeptide can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application The preparation according to the present invention can be made available as a pharmaceutical preparation with FVII activity in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

The pharmaceutical protein preparation may be used at dosages of between 30-270 μg/kg as single daily injection or up to 3 times/day for several days. Patients may be treated immediately upon presentation at the clinic with a bleed. Alternatively, patients may receive a bolus infusion every eight to twelve hours, or if sufficient improvement is observed, a once daily infusion of the variant FVII polypeptide described herein. Dosing will be determined by indication and prescribed by the treating physician.

B. Variant FVII-Encoding Nucleic Acids

Variant FVII-encoding nucleic acids may be used for a variety of purposes in accordance with the present invention. In a preferred embodiment of the invention, a nucleic acid delivery vehicle (i.e., an expression vector) for modulating blood coagulation is provided wherein the expression vector comprises a nucleic acid sequence coding for a variant FVII polypeptide, or a functional fragment thereof as described herein. Administration of FVII-encoding expression vectors to a patient results in the expression of variant FVII polypeptide which serves to alter the coagulation cascade. In accordance with the present invention, a variant FVII encoding nucleic acid sequence may encode an FVII polypeptide as described herein whose expression increases hemostasis. In a preferred embodiment, a variant FVII nucleic acid sequence encodes a human FVII polypeptide variant with altered EPCR binding affinity.

Expression vectors comprising variant FVII nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible compositions.

In a preferred embodiment of the invention, the expression vector comprising nucleic acid sequences encoding the variant FVII polypeptides is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-1 to AAV-12, and others) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, retroviral vectors, lentiviral vectors, non-viral vectors and others.

In a preferred embodiment of the present invention, methods are provided for the administration of a viral vector comprising nucleic acid sequences encoding a variant FVII polypeptide, or a functional fragment thereof. AAV vectors and lentiviral vectors have broad utility in the methods of the present invention and preferably do not include any viral genes associated with pathogenesis. Most preferably, only the essential parts of vector e.g., the ITR and LTR elements, respectively are included. Direct delivery of vectors or ex-vivo transduction of human cells and followed by infusion into the body will result in expression of variant FVIIas thereby exerting a beneficial therapeutic effect on hemostasis. Recombinant AAV and lentiviral vectors have found broad utility for a variety of gene therapy applications. Their utility for such applications is due largely to the high efficiency of in vivo gene transfer achieved in a variety of organ contexts.

AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. It is likely that non-viral vectors based on plasmid DNA or minicircles will be also suitable gene transfer vectors for a large gene as that encoding variant FVII.

It is desirable to introduce a vector that can provide, for example, multiple copies of a desired gene and hence greater amounts of the product of that gene. Improved AAV and lentiviral vectors and methods for producing these vectors have been described in detail in a number of references, patents, and patent applications, including: Wright J. F. (Hum Gene Ther 20:698-706, 2009) which is the technology used for the production of clinical grade vector at our facility at Children's Hospital of Philadelphia (CHOP). Lentiviral vector can be produced at CHOP and the other vectors are available through the Lentivirus vector production core laboratory by NHLBI Gene Therapy Resource Program (GTRP)—Lentivirus Vector Production Core Laboratory. For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant FVII or functional fragments thereof. For example, nucleic acid sequences encoding variant FVII under the control of a cytomegalovirus (CMV) promoter can be employed for skeletal muscle expression or the hAAT-ApoE and others for liver specific expression. Hematopoietic specific promoters in lentiviral vectors may also be used to advantage in the methods of the present invention.

Exemplary Methods for Producing AAV vectors

AAV for recombinant gene expression have been produced in the human embryonic kidney cell line 293 and extensively recently reviewed by the Director of Clinical Vector Core at CHOP, Dr. J. F. Wright (Hum Gene Ther 20:698-706, 2009). Briefly, AAV vectors are engineered from wild-type AAV, a single-stranded DNA virus that is non-pathogenic. The parent virus is non-pathogenic, the vectors have a broad host range, and they can infect both dividing and non-dividing cells. The vector is engineered from the virus by deleting the rep and cap genes and replacing these with the transgene of interest under the control of a specific promoter. For recombinant AAV preparation, the upper size limit of the sequence that can be inserted between the two ITRs is ~5.0 kb. The plasmids expressing variant FVII (of mammalian origin) under the control of a regulatory element that directs expression to the desired tissue and a second plasmid supplying adenovirus helper functions along with a third plasmid containing the AAV-2 rep and cap genes were used to produce AAV-2 vectors, while a plasmid containing either AAV-1, AAV-6, or AAV-8 cap genes and AAV-2 rep gene and ITR's are used to produce the respective alternate serotype vectors (Gao et al., (2002) Proc. Natl Acad. Sci. USA 99:11854-11859; Xiao et al., (1999) J. Virol. 73:3994-4003; Arruda et al., (2004) Blood 103:85-92). AAV vectors are purified by repeated CsCl density gradient centrifugation and the titer of purified vectors determined by quantitative dot-blot hybridization or by silver stain of viral capsid proteins against a known control.

Also included in the present invention is a method for modulating hemostasis comprising providing cells of an individual with a nucleic acid delivery vehicle encoding a variant FVII polypeptide and allowing the cells to grow under conditions wherein the FVII polypeptide is expressed.

From the foregoing discussion, it can be seen that FVII polypeptides, and FVII polypeptide expressing nucleic acid vectors may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., a variant FVII polypeptide or functional fragment or derivative thereof) or by inducing continuous expression of the variant FVII transgene in vivo by gene- and or cell-based therapies or by ex-vivo modification of the patient's or donor's cells. In a particular embodiment of the present invention, pharmaceutical compositions comprising sufficient genetic material to enable a recipient to produce a therapeutically effective amount of a variant FVII polypeptide can influence hemostasis in the subject. Alternatively, as discussed above, an effective amount of the variant FVII polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of variant FVII-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant FVII polypeptide. Thus, a therapeutically effective amount in humans will fall in a relatively broad range that may be determined by a medical practitioner based on the response of an individual patient to vector-based FVII treatment.

D. Administration

The variant Factor VII polypeptides, alone or in combination with other agents may be directly infused into a patient in an appropriate biological carrier as described hereinabove. Expression vectors of the present invention comprising nucleic acid sequences encoding variant FVII, or functional fragments thereof, may be administered to a patient by a variety of means (see below) to achieve and maintain a prophylactically and/or therapeutically effective level of the FVII polypeptide. One of skill in the art could readily determine specific protocols for using the FVII encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

Variant FVII encoding adenoviral or adeno-associated vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising FVII nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant FVII polypeptide.

Also provided are lentivirus or pseudo-typed lentivirus vectors comprising a nucleic acid sequence encoding a variant FVII polypeptide.

Also encompassed are naked plasmid or expression vectors comprising a nucleic acid sequence encoding a variant FVII polypeptide.

The following example is provided to illustrate certain embodiments of the invention. It is not intended to limit the invention in any way.

EXAMPLE I

Modulation of FVIIa Interaction with Endothelial Protein C Receptor as Means to Improve the Hemostatic Effects of FVIIa The mode of action of high dose rFVIIa is not well understood but it involves multiple cellular as well as protein components of the coagulation system. Under therapeutic protein administration, activated FVII (FVIIa) can directly activate coagulation factor X (generating Factor Xa), resulting in thrombin generation and clot formation. FVIIa's natural cofactor is tissue factor (TF) that, when exposed to the circulation following injury, localizes the FVIIa coagulant reactions. However, the contribution of this pathway in hemophilia following FVIIa treatment is not entirely delineated. On the other hand, FVIIa has also been shown to interact with a cellular receptor (endothelial protein C receptor, EPCR) on the surface of endothelial cells that line blood vessels. The physiological ligand for EPCR, protein C is utilized to boost the anticoagulant protein C pathway that controls excessive coagulation. Given these data, it is possible that following pharmacologic FVIIa administration in patients, FVIIa may bind EPCR further localizing FVIIa on the endothelium where it can potentially participate in procoagulant reactions (with or without tissue factor) in addition to those occurring on activated platelets (mechanism #1). Alternatively or in addition to the above mode of action, FVIIa binding to EPCR may interfere (downregulate) the anticoagulant pathway (mechanism #2). These mechanisms either by themselves or combined, can result in the net beneficial hemostatic effects observed following rFVIIa administration.

Figure 2A:
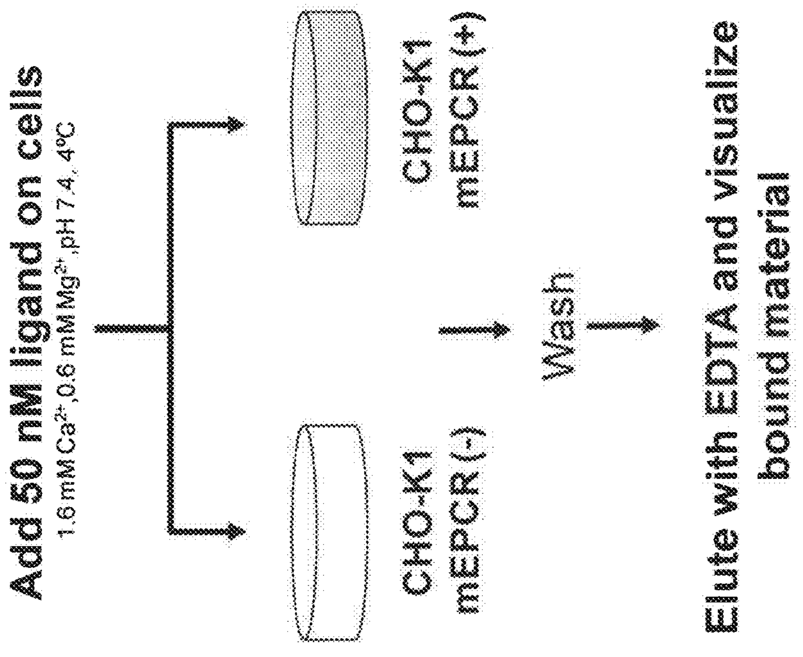
FIG. 2A: Scheme for determining and quantifying binding of proteins to surface exposed mouse EPCR (mEPCR). The protein whose mEPCR binding is under investigation is added onto CHO-K1 cells expressing mEPCR (mEPCR+ve) or not (mEPCR−ve). Binding is done in the presence of physiological concentration of calcium and magnesium (1.6 mM and 0.6 mM, respectively). Following washing, the bound material is eluted with EDTA (10 mM). The bound, unbound and a portion of total loaded material are then subjected to polyacrylamide gel electrophoresis, transferred to nitrocellulose and detected by western blotting using protein-specific antibodies.
Figure 2B:
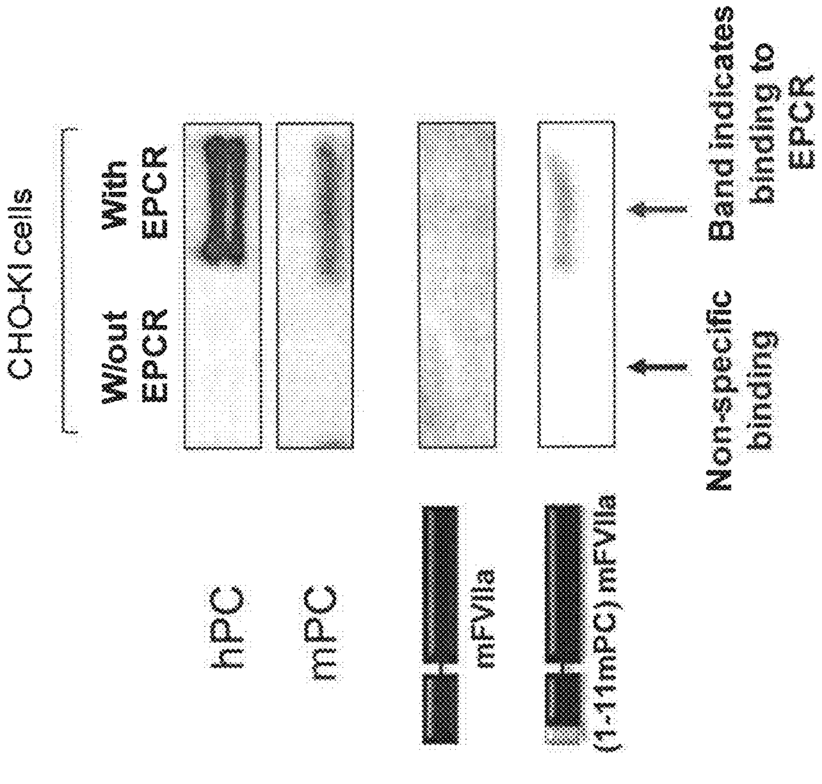
FIG. 2B: Human plasma-derived protein C (hPC) or murine PC (mPC) that are known ligands for murine EPCR, were incubated with CHO-K1 cells with or without murine EPCR expression. Western blot analysis showed detectable and specific binding of either ligand on cells expressing murine EPCR. In contrast, mFVIIa showed no detectable binding. A variant mFVIIa bearing part of the mPC Gla domain ([1-11 mPC]-mFVIIa) restored binding of this chimeric molecule to murine EPCR.
Figure 3:
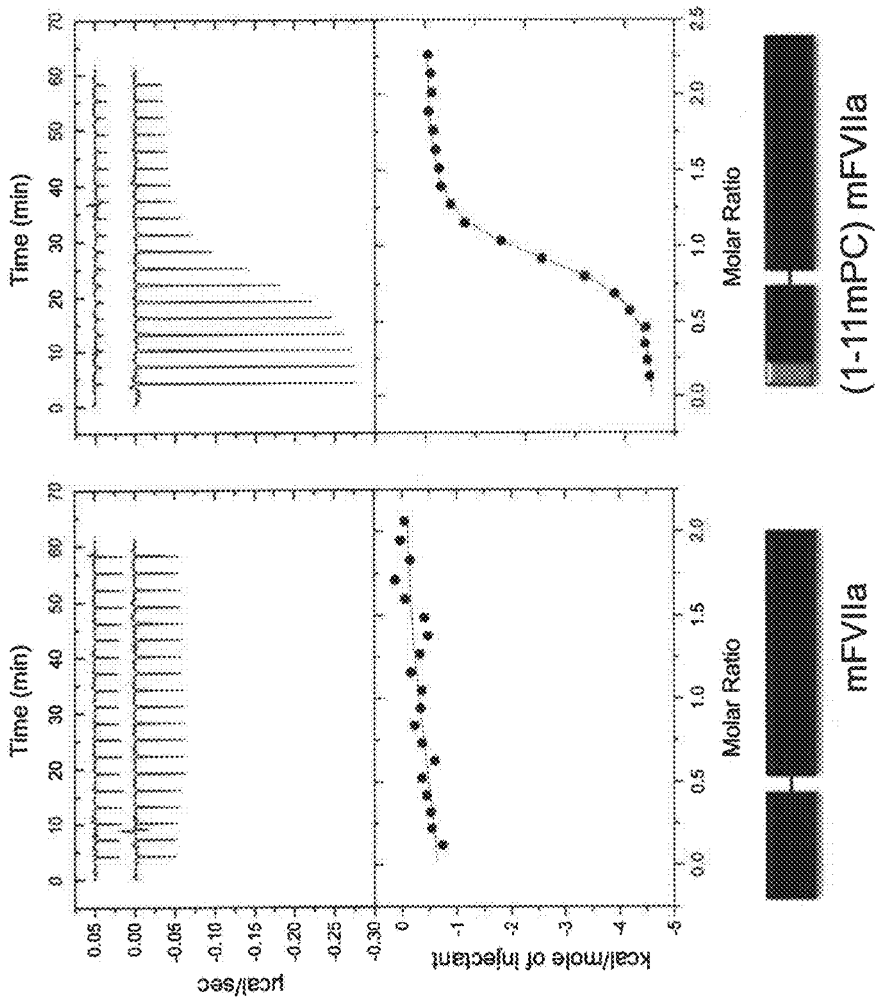
FIG. 3. In isothermal titration calorimetry, ligand and murine EPCR (soluble) are mixed and the heat generated from direct interaction is measured and plotted vs. molar ratio of receptor/ligand. The resulting isotherm is used to calculate both the stoichiometry and the Kd of the interaction. As can be seen, mFVIIa showed no interaction (Kd>8 μM) in contrast to [1-11 mPC]-mFVIIa (Kd~480 nM).

Existing data seem to suggest that the binding of FVIIa to EPCR results in the rapid sequestration of the FVIIa molecule away from the blood stream, thereby reducing its circulatory half-life. For example, in mouse experiments, administration of human FVIIa in mice overexpressing EPCR or in mice deficient in EPCR resulted in enhanced or impaired biodistribution of FVIIa (Clark C A et al., J Thromb Haemost 2012). We have generated a series of data that support the sequestration of FVIIa from the circulation but using an entirely mouse system. We generated a mouse version of FVIIa using a PACE furin cleavage site between the light and heavy chains of mouse FVII (Margaritis P, J Clin Invest 2004). In this molecule, cleavage inside the cell (via the PACE furin site) results in a molecule that is secreted in its activated, two chain form. We demonstrated that mouse FVIIa (mFVIIa) has very weak interaction (in the μM range) with mouse EPCR (mEPCR) using methodology shown in FIG. 2A. This was shown using mouse FVIIa, on cells that express the mouse EPCR receptor (mEPCR, FIG. 2B) as well as using a solution-based assay (isothermal titration calorimentry) and measuring the interaction of mFVIIa with soluble mEPCR (FIG. 3).

Figure 4A:
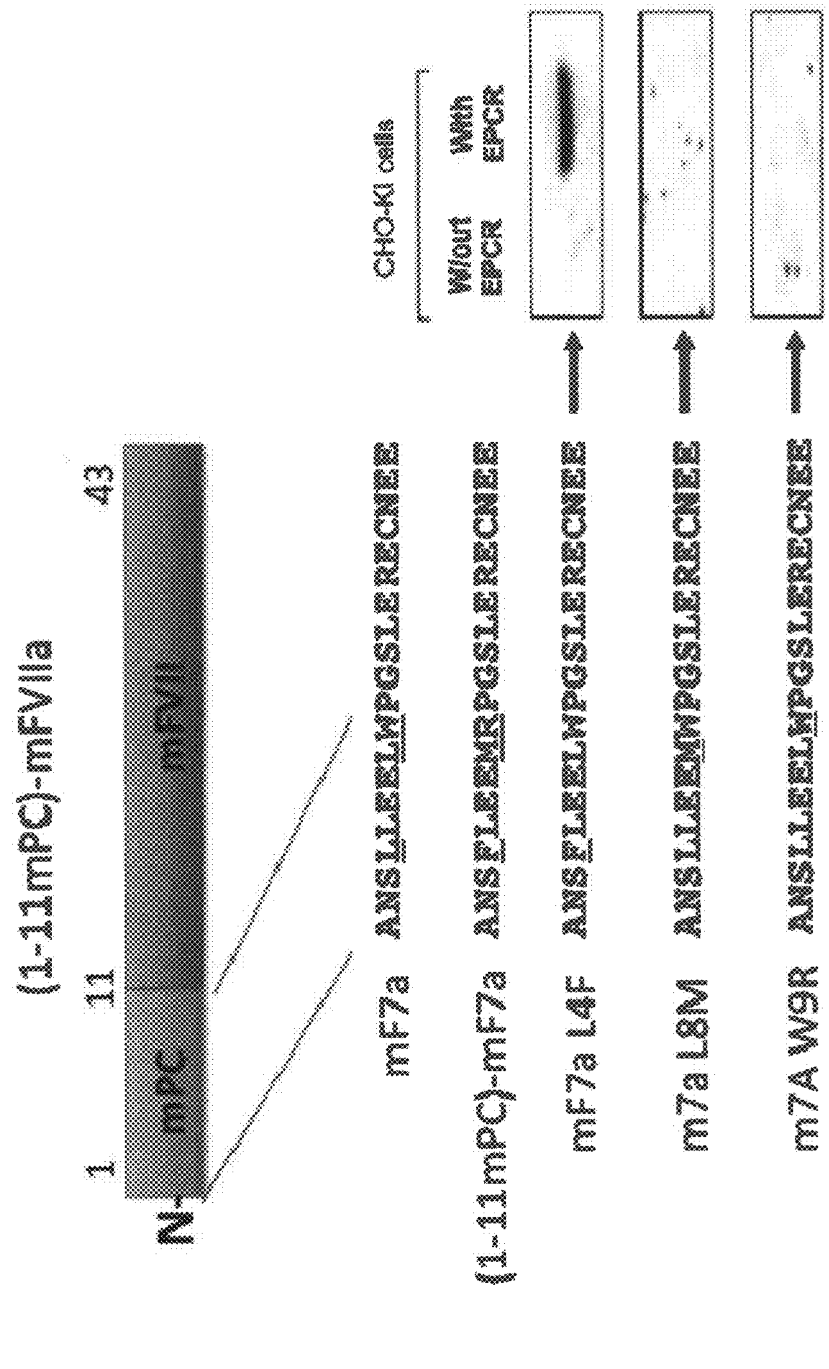
FIG. 4A: The Gla domain of the (1-11 mPC)-mFVIIa is shown. The blue box represents the first 11 amino acids of the mouse PC (mPC) Gla domain, whereas the red box represents the portion of the Gla domain of mouse FVIIa. Sequence alignment of mFVIIa and (1-11 mPC)-mFVIIa shows 3 amino acid differences, shown in red text and underlined. Individual mutations were performed to change one amino acid in mFVIIa with the corresponding in (1-11 mPC)-mFVIIa. Following transient expression in HEK-293 cells, supernatant with each protein was incubated with CHO-K1 cells with or without expression of the mouse EPCR receptor. Analysis of binding shows that position 4 in the mPC Gla domain is responsible for mEPCR binding since a Leu to Phe in mFVIIa at that position (i.e. same as in mPC) allows mFVIIa to bind mEPCR. From top to bottom, sequences are SEQ ID NOs: 1-5.
Figure 4B:
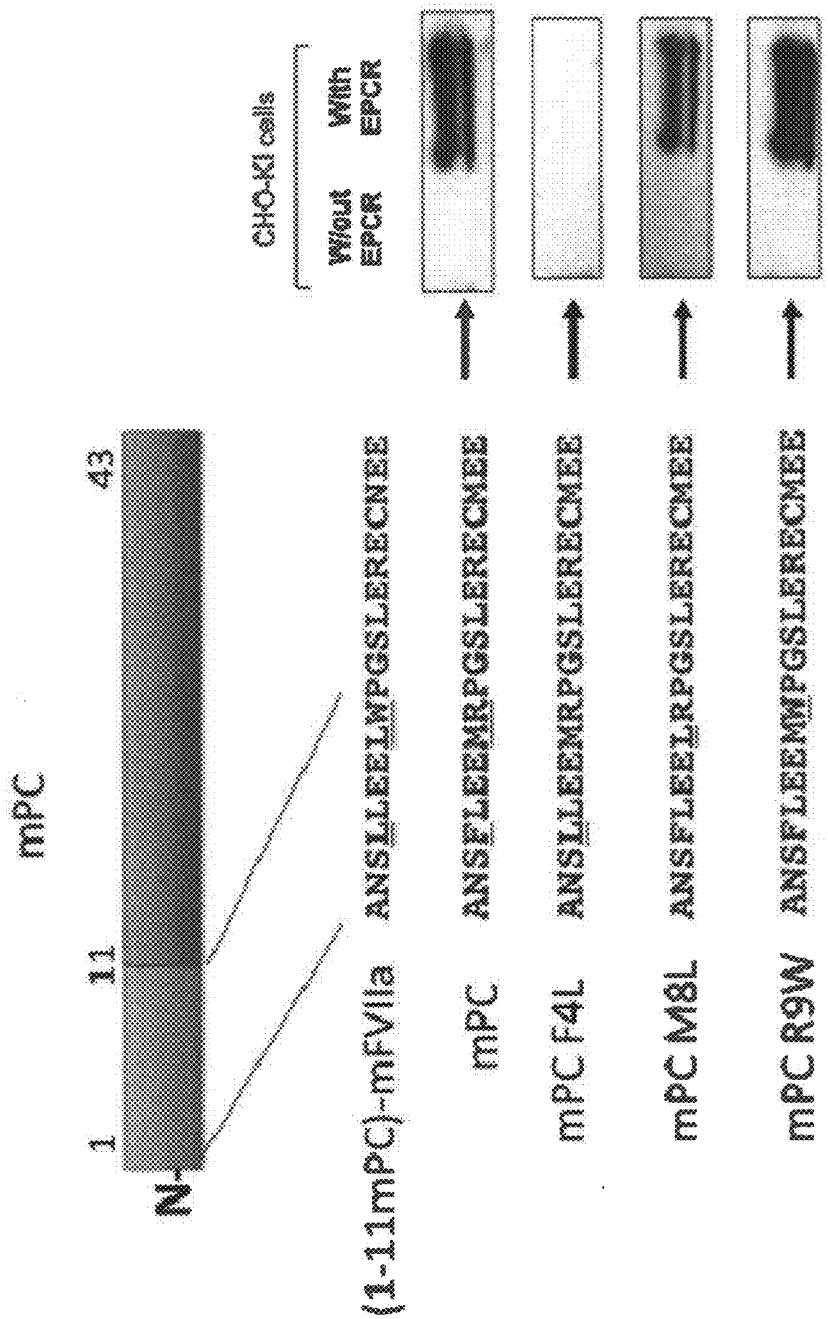
FIG. 4B: The Gla domain of mouse PC is shown. The blue box represents the portion of this Gla domain that was transplanted to (1-11 mPC)-mFVIIa. Within that region, three amino acids are different between mouse PC and mFVIIa, shown in red text. Individual mutations were performed to change each position to the one present in mFVIIa. Following transient expression in HEK-293 cells, supernatant with each protein was incubated with CHO-K1 cells with or without expression of the mouse EPCR receptor. Analysis of binding shows that mutating position 4 to the amino acid in mFVIIa (Phe to leu) abrogates binding of mouse PC to mouse EPCR, confirming the observations seen in FIGS. 2 and 3. From top to bottom, sequences are SEQ ID NOs: 1 and 6-9.
Figure 7:
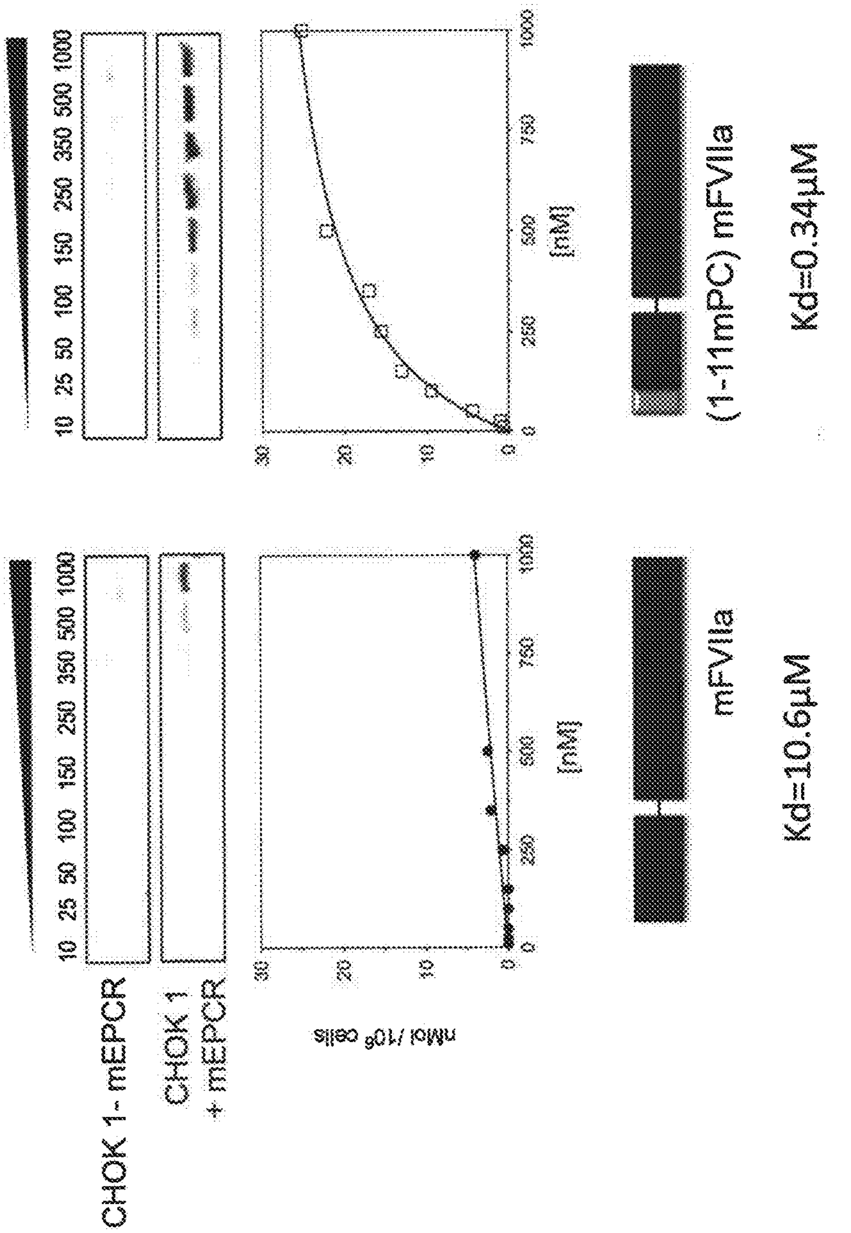
FIG. 7. Increasing concentration of ligand (mFVIIa or [1-11 mPC]-mFVIIa) was incubated with CHO-K1 cells without mEPCR (−mEPCR) or with mEPCR (+mEPCR). The experimental strategy described in Example I was followed and bound material was visualized. Following subtraction of non-specific binding (material incubated on CHO-K1 [−]mEPCR cells), corrected amount of bound material (nM per $10^6$ cells) was plotted vs. concentration of ligand (nM). Fitting of data allowed for determination of Kd, shown under each graph.

The lack of interaction of mFVIIa to mEPCR makes the mouse the ideal animal model to study hemostatic effects from the FVIIa-EPCR interaction (endogenous mFVII/mFVIIa does not interact to mEPCR i.e. there is zero background). To do this, we generated a variant of mouse FVIIa that has a portion of its Gla domain substituted with those of mouse protein C (the Gla domain is where interaction occurs to EPCR; protein C is the physiological ligand of EPCR). This variant ([1-11 mPC]-mFVIIa) shown in FIG. 1 only harbors 3 amino acid changes vs. mFVIIa (Leu4 to Phe, Leu8 to Met and Trp9 to Arg) demonstrated that it bound mouse EPCR on the cell surface (FIG. 2B) as well as in solution using isothermal titration calorimetry (FIG. 3). For this molecule, EPCR binding capacity is a gain of function, relative to mouse FVIIa. Using cells that either express or do not express mEPCR and incubating increasing concentration of either mFVIIa or (1-11 mPC)-mFVIIa, we determined a Kd of interaction of the ligand to the full-length receptor (FIG. 7). The data were comparable to the data obtained from experiments in solution. Further experimentation identified the amino acid that confers the capacity to bind EPCR as that in position 4 in the mature polypeptide (either in mFVIIa or in murine protein C). A Phe residue instead of the normal Leu residue (Leu to Phe) converts mouse FVIIa from a non-binder to a binder for mouse EPCR (mF7a L4F, FIG. 4A). This was also confirmed by doing the reverse experiment: mutating the amino acid at position 4 in mouse PC (EPCR binder) with the one in mouse FVIIa (i.e. Phe to Leu) converted mouse PC from an EPCR binder to a non-binder (mPC F4L, FIG. 4B).

Figure 5A:
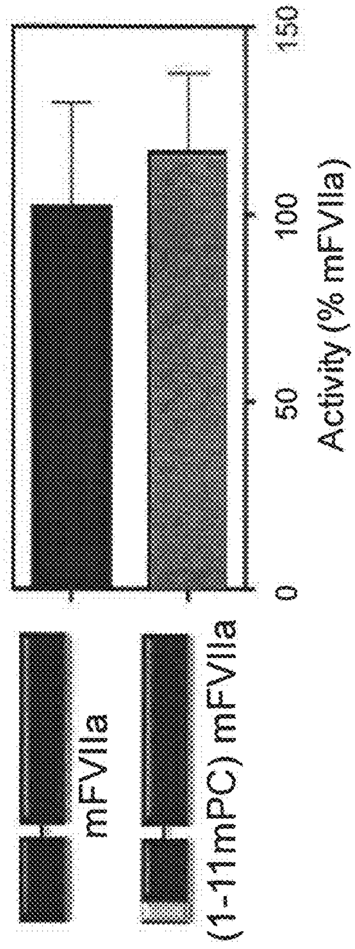
FIG. 5A: Either mFVIIa or (1-11 mPC)-mFVIIa were used in a TF-based clotting assay that measures coagulant activity. Data are shown as activity (% of mFVIIa) and both proteins exhibit similar activity.
Figure 5B:
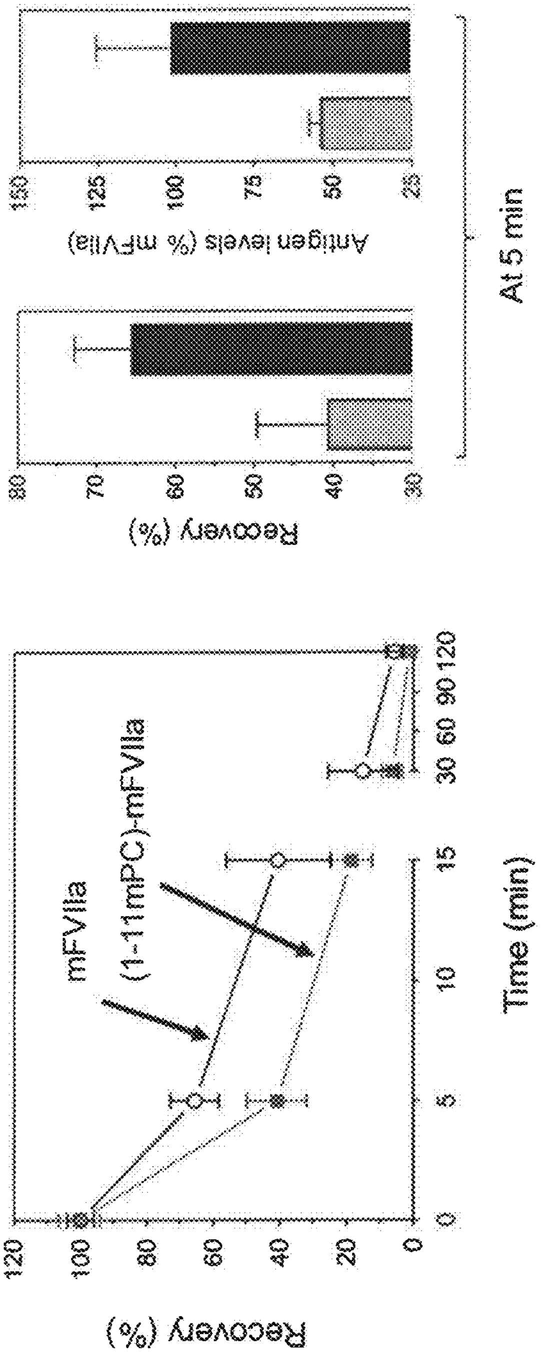
FIG. 5B: Following administration of either mFVIIa or (1-11 mPC-mFVIIa) in mice, we measured remaining protein in circulation (recovery), shown as % of infused amount. At 5 min post-infusion, the (1-11 mPC)-mFVIIa levels (grey) (% recovery and antigen levels [% of mFVII]) were ~2 fold lower than those of mFVIIa (black).
Figure 8:
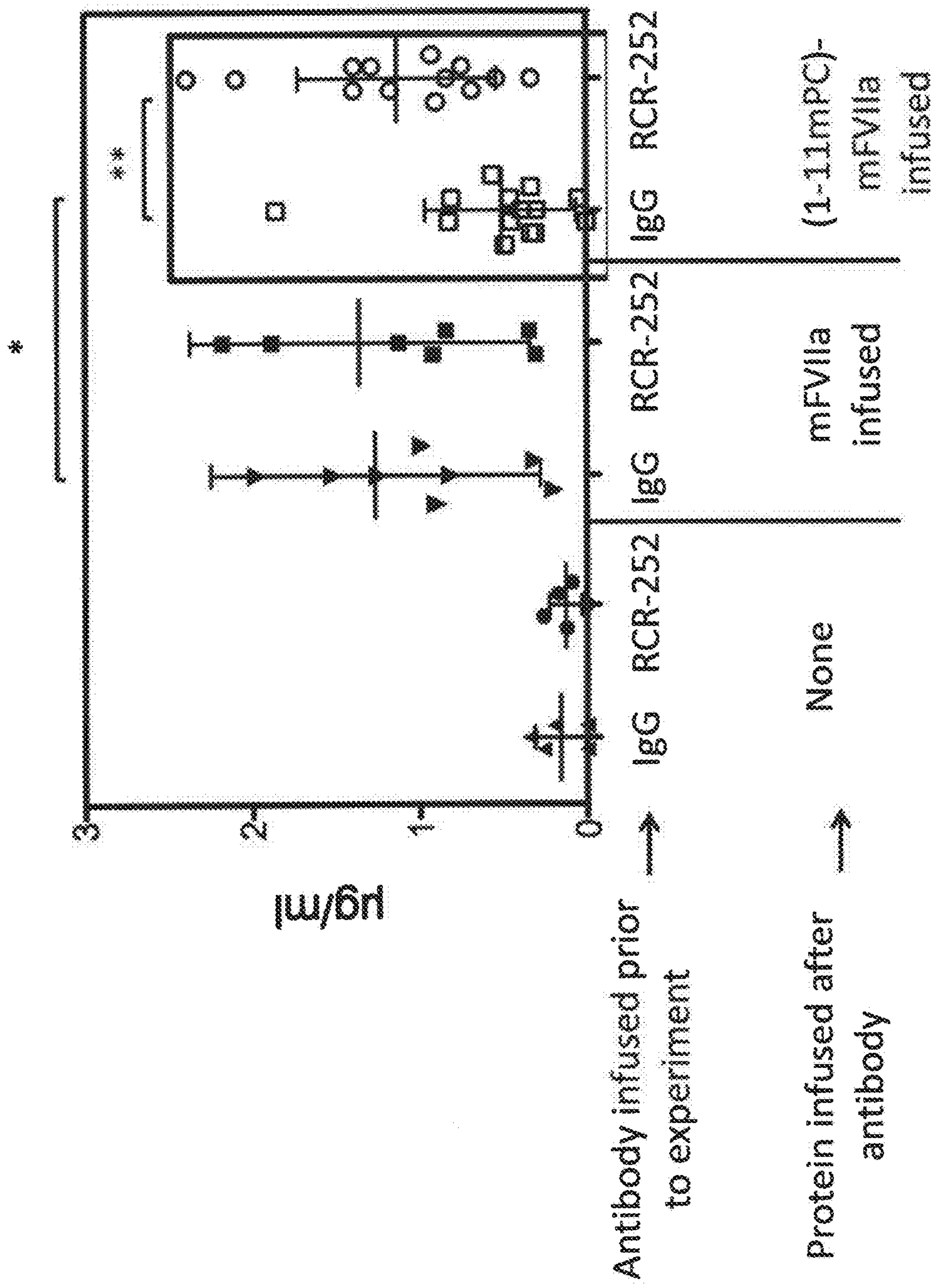
FIG. 8. Either isotype IgG or a blocking anti-mEPCR antibody (RCR-252) was infused in normal mice. One hour later, either mFVIIa or (1-11 mPC) were infused in those mice (or no protein in control mice that had otherwise received IgG or RCR-252). Either mFVIIa or (1-11 mPC)-mFVIIa was infused at equal amounts and all mice had similar body weights. At 5 minutes post protein infusion, blood was collected and protein concentration in plasma was quantified (as described in Margaritis et al., Blood 2011). Mice that received no protein other than IgG or RCR-252 had similar levels of mFVIIa (i.e. denotes background levels of mFVIIa in normal mice). Infusion of IgG or RCR-252 did not change the concentration of infused mFVIIa, confirming that the measured concentration of mFVIIa following its infusion was independent of mEPCR binding. As expected (see FIG. 5B), mice that received IgG and (1-11 mPC)-mFVIIa showed reduced circulating levels vs. mFVIIa (*$P<0.05$). However, blocking mEPCR binding with RCR-252 and subsequent infusion of (1-11 mPC)-mFVIIa resulted in better recovery of the infused protein (greater concentration in plasma, red box), **$P<0.01$. The concentration of (1-11 mPC)-mFVIIa in the RCR-252 group was similar to mFVIIa (on either IgG or RCR-252 group).
Figure 10B:
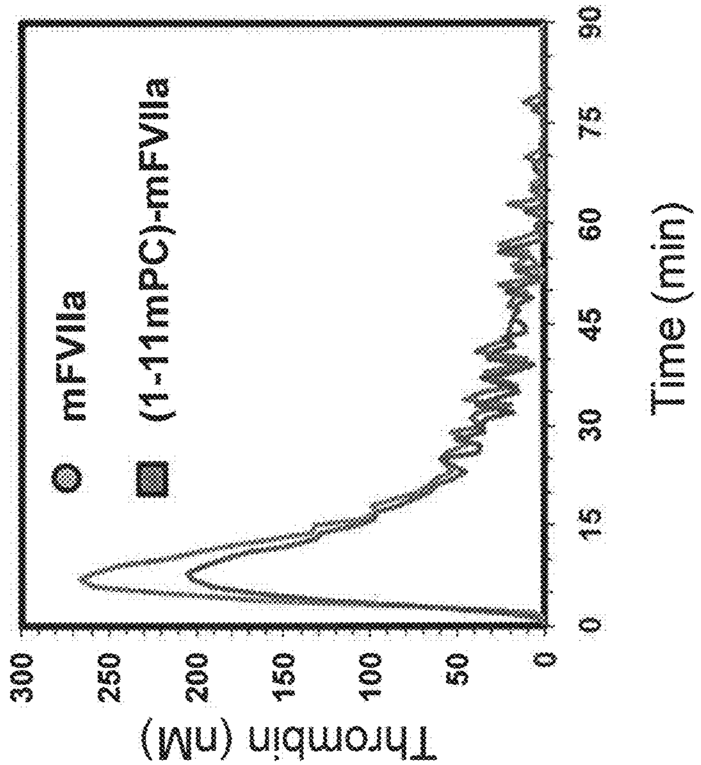
FIG. 10B: We performed a thrombin generation assay in hemophilia B mouse plasma, following addition of identical amounts of mFVIIa or mFVIIa-FMR. Initiation of coagulation was by adding a mixture of TF and phospholipids. A representative graph of thrombin (nM) generation as a function of time is shown. No statistical differences were observed between the two proteins.
Figure 10A:
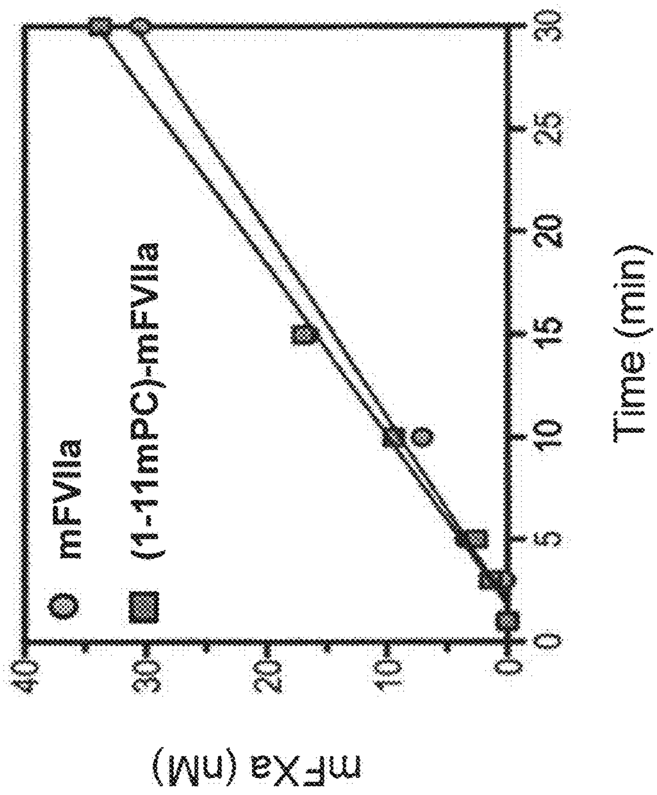
FIG. 10A: CHO-K1 cells expressing full-length murine TF were generated. On such cells, we added mFVIIa or mFVIIa-FMR and measured the proteolytic activity of the binary complex (mFVIIa:mTF or mFVIIa-FMR:mTF) towards murine Factor X, expressed as nM of mFXa generated as a function of time. Both mFVIIa and mFVIIa-FMR had similar rates of mFXa generation (slope).

In addition to its mouse EPCR binding capacity, the (1-11 mPC)-mFVIIa variant had normal coagulant activity (FIG. 5A). Also, both mFVIIa and (1-11 mPC)-mFVIIa exhibited similar tissue factor-dependent proteolytic and coagulant activities, as evidenced by murine FXa generation on CHO-K1 cells expressing murine tissue factor and by a thrombin generation assay in mouse hemophilic plasma (FIG. 10A and B, respectively). These results suggest that these two properties can co-exist in the same molecule. We subsequently administered equal amount of mouse FVIIa or [1-11 mPC]-mFVIIa to age and weight matched wildtype mice. At different time points, we collected blood and assayed the recovery of the infused protein using a clotting based assay. We observed that the [1-11 mPC]-mFVIIa was rapidly sequestered from the circulation, with almost 50% less protein present at 5 min (FIG. 5B). To determine whether EPCR binding was responsible for the reduced recovery of (1-11 mPC)-mFVIIa, we used a blocking anti-murine EPCR antibody prior to infusion of [1-11 mPC]-mFVIIa. We subsequently measured recovery at 5 min after [1-11 mPC]-mFVIIa infusion. Infusion of the EPCR blocking antibody resulted in better recovery of (1-11 mPC)-mFVIIa vs. no anti-EPCR antibody), similar to the recovery observed with mFVIIa (FIG. 8). This result confirms the reduced recovery of [1-11 mPC]-mFVIIa being dependent on its specific binding to murine EPCR. What differentiates our data from existing reports is the use of a gain-of-function variant of mouse origin infused in a completely "physiological" environment (mouse protein infused in a mouse). This avoids species incompatibilities that may have affected previous published reports. As such, our data clearly demonstrate that changing EPCR binding capacity of FVIIa can result in molecule(s) with altered in pharmacokinetic profile(s).

Figure 9A:
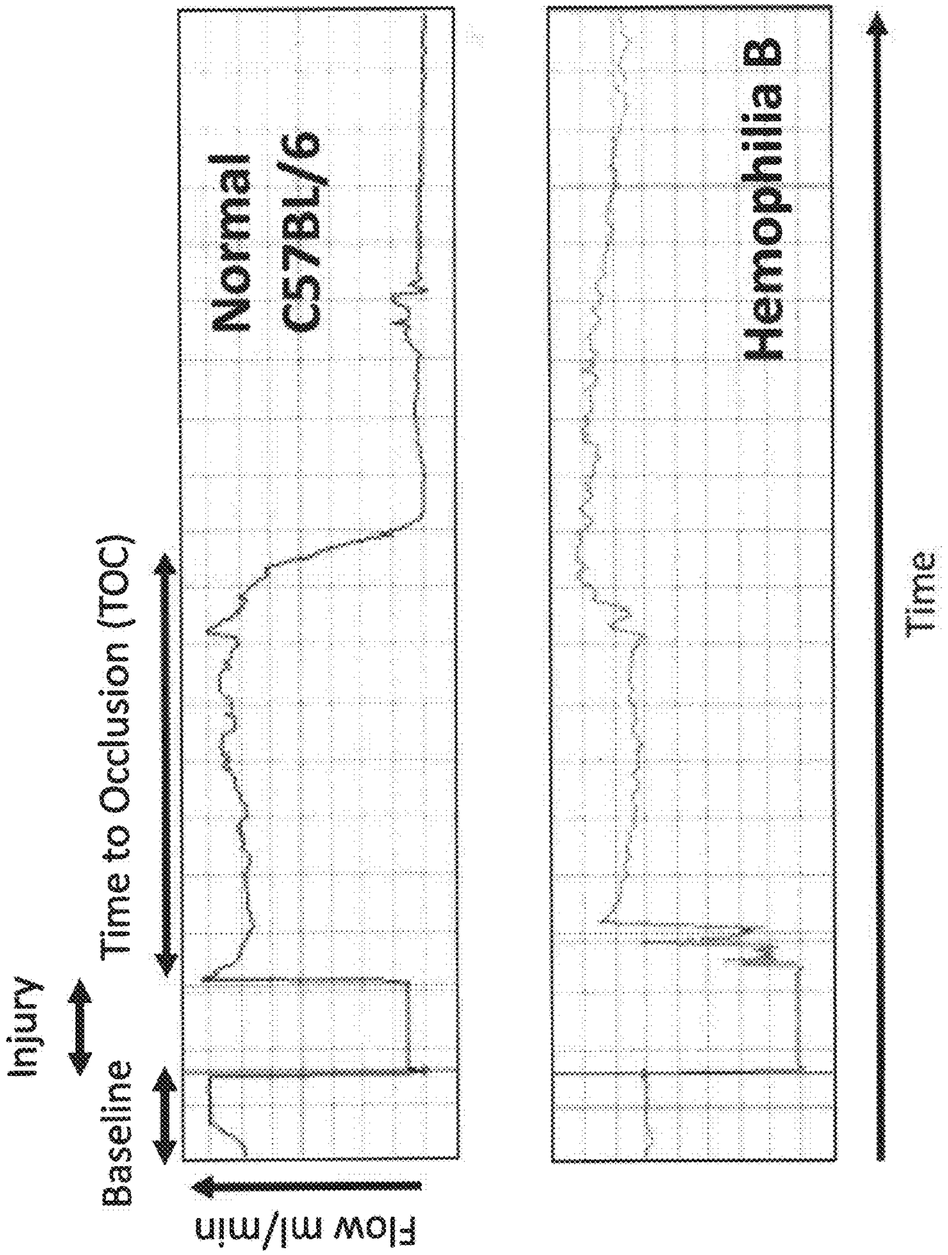
FIG. 9A: A Doppler probe is placed under the carotid artery of a mouse and measures baseline blood flow (ml/min). An injury (7.5% $FeCl_3$ for 2 min) is performed and, following that, time to vessel occlusion is determined (no flow). Normal mice occlude within 15 minutes whereas hemophilia B mice show no occlusion throughout the observation period of 30 minutes.
Figure 9B:
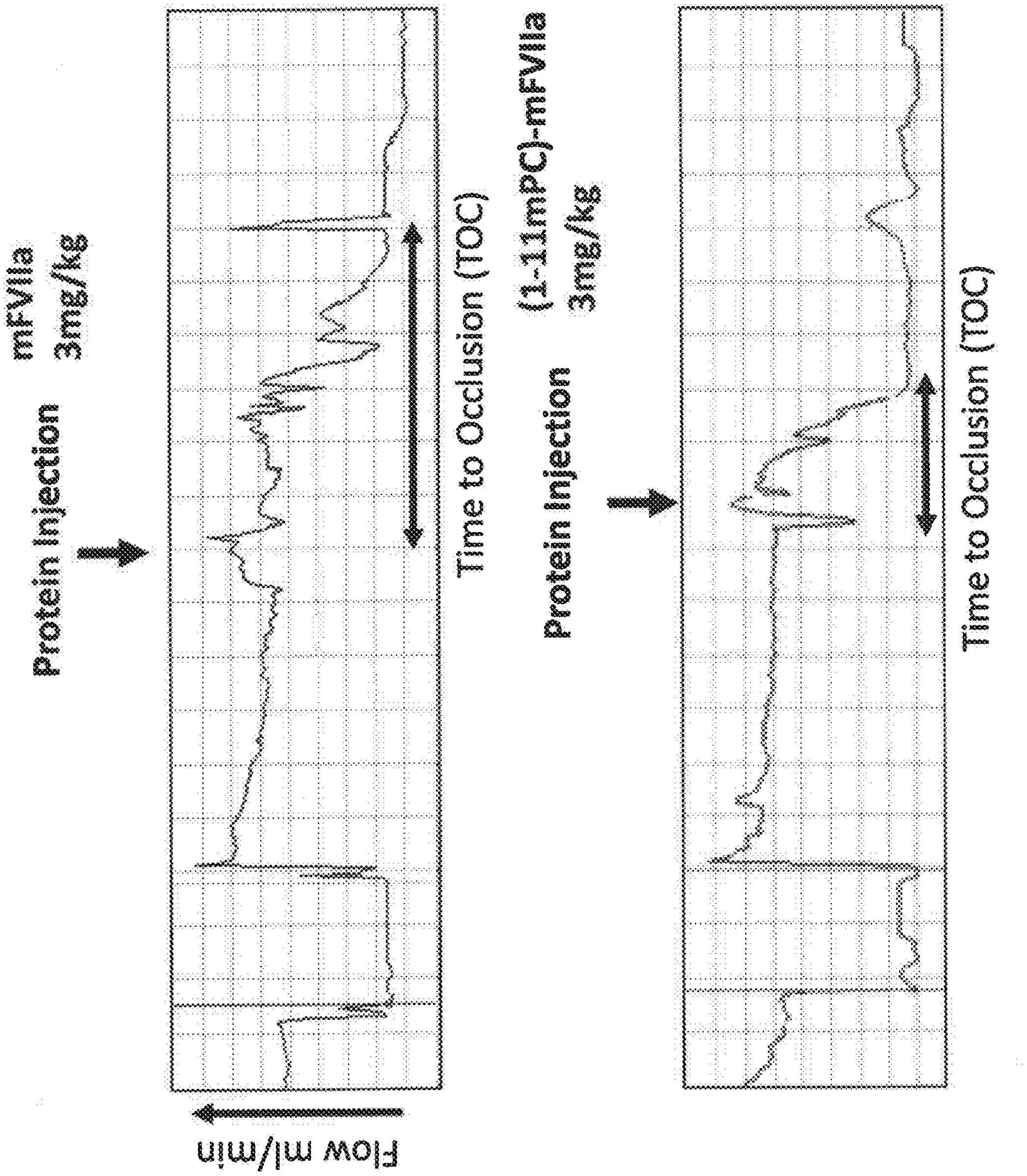
FIG. 9B: An example of hemostatic effect of either mFVIIa or (1-11 mPC)-mFVIIa infusion in hemophilia B mice in the $FeCl_3$ model. Following baseline blood flow and injury of hemophilia B mice, we monitored a steady blood flow for 10 minutes. Infusion of mFVIIa or (1-11 mPC)-mFVIIa at 3 mg/kg resulted in vessel occlusion with mice receiving (1-11 mPC)-mFVIIa showing faster vessel occlusion than those receiving mFVIIa.
Figure 11:
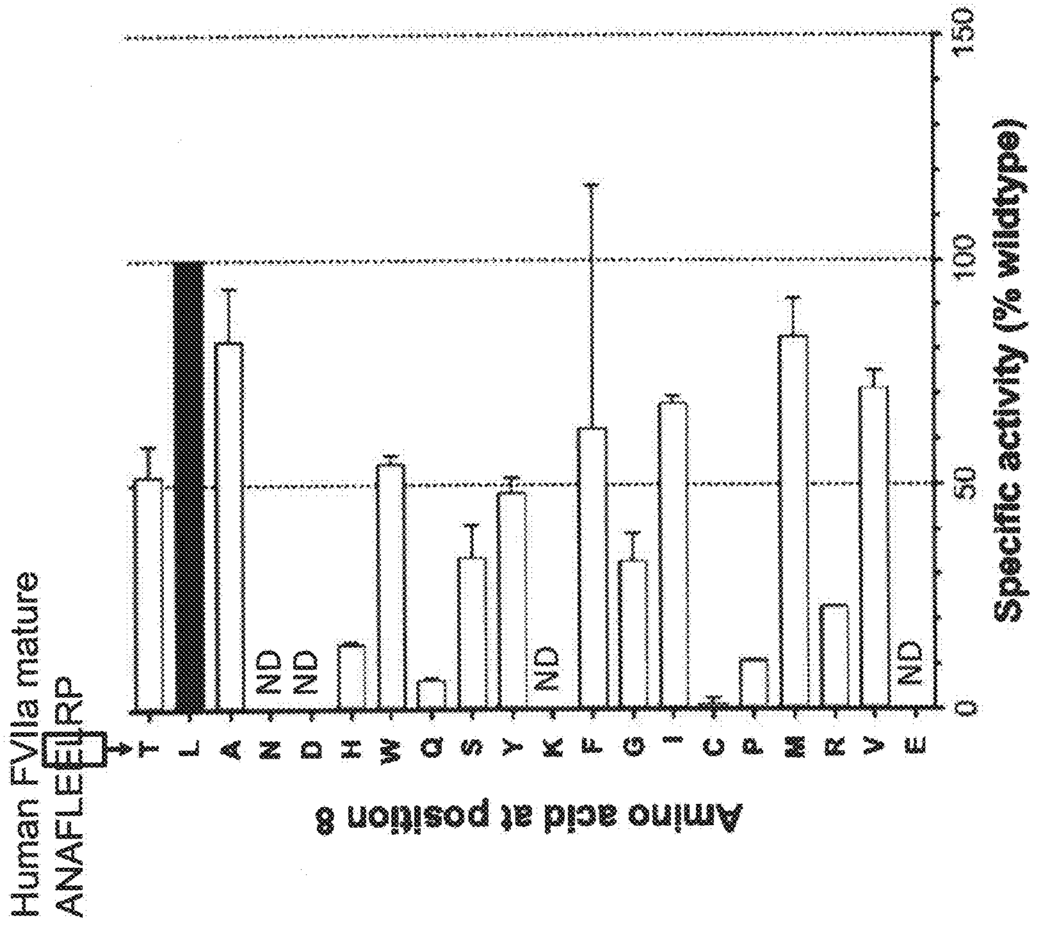
FIG. 11. Specific activity of variants of human FVIIa, following transient transfection. Human embryonic kidney cells 293 (HEK-293) were transiently transfected with plasmids containing the human FVIIa DNA sequence coding for amino acid mutations at position 8 of the mature, secreted wildtype human FVIIa protein. This position is shown surrounded by a red box and the normal (wildtype) amino acid at position 8 is Leu. All constructs contained a PACE/furin cleavage site (ArgLysArg-ArgLysArg; SEQ ID NO: 11), as we have previously described (Margaritis P. et al., J Clin Invest 2004). One plasmid construct was used per transfection. Transfection took place in the presence of vitamin K and, 48 h later, culture medium was collected and analyzed for activity and antigen, using wildtype (black bar, Leu) as 100%. Specific activity is defined as the ratio of clotting activity/antigen for each construct. Each mutated amino acid in the plasmid constructs tested is shown using the single letter amino acid code. ND: none detected FIG. 12. Binding of variants of human activated FVII with amino acid changes at position 8 (normally a Leucine). Conditioned medium from transient transfection was added on CHO-K1 cells expressing human EPCR, as described in FIG. 2. The top image shows the amount loaded on these cells, as visualized by western blotting (Load). Following the wash of unbound material, the bound fraction was visualized by western blotting (shown in the bottom image). The presence of a band in the bound fraction indicated that the particular FVII molecule bound human EPCR. Leu (the wildtype amino acid) and Ile at position 8 exhibited detectable binding to human EPCR. Human FVIIa (NovoSeven) is shown as a control for positive binding. The single amino acid code is used to designate the particular human FVII polypeptides tested.
Figure 12:
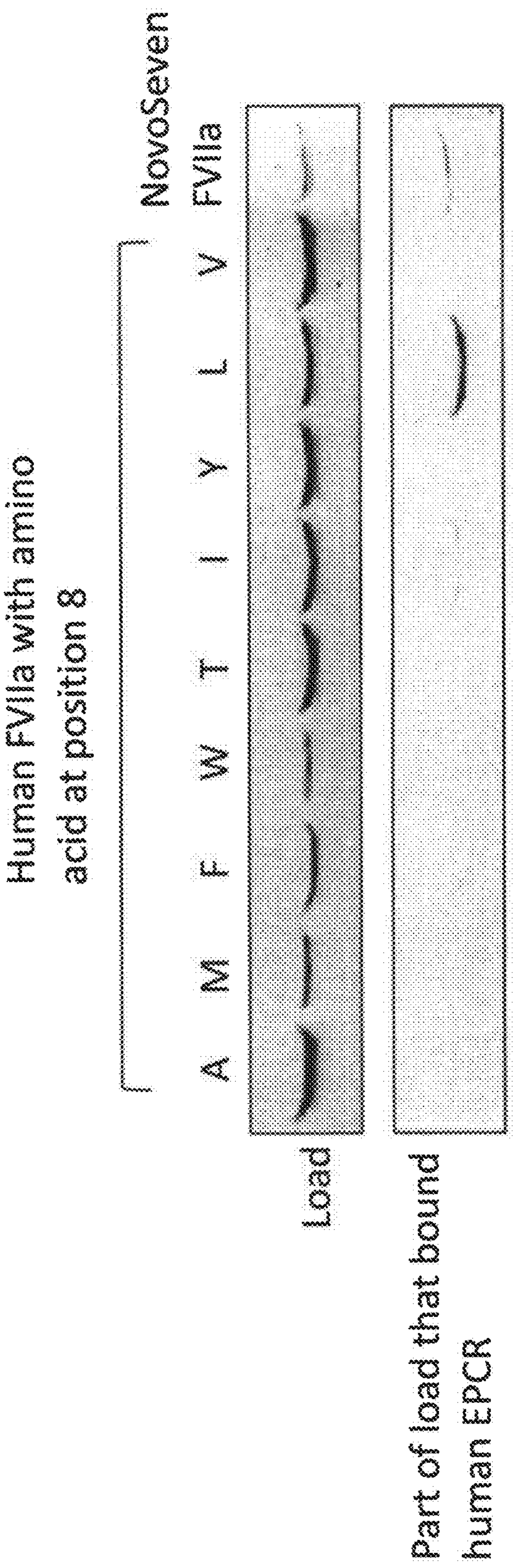

An example of how altering the EPCR binding capacity of FVIIa can influence a hemostatic outcome is shown using an injury model of the carotid artery in hemophilic mice. This large diameter vessel was chosen since EPCR density increases with vessel diameter. The injury model relies on measuring blood flow through the carotid artery prior to and after an injury is performed using ferric chloride (the injury is applied for 2 minutes). Full occlusion of the vessel as a result of thrombus formation will result in stopping of blood flow (FIG. 9A). In our particular experimental conditions, wild type mice (normal hemostasis) show full occlusion of the carotid (no blood flow) within 15 minutes following the injury. In contrast, hemophilia mice (defective hemostasis) show no vessel occlusion throughout the observation period of the experiment (30 minutes). Using hemophilic mice, we infused different doses of either mFVIIa or [1-11 mPC]-mFVIIa after the injury was made and measured blood flow. We found that the [1-11 mPC]-mFVIIa at every dose administered resulted in enhanced hemostasis (vs. mFVIIa at the same dose) as shown in Table 1. At a mFVIIa dose that normalized the time to vessel occlusion (3 mg/kg), the same dose of (1-11 mPC)-mFVIIa resulted in a significantly enhanced hemostatic response with a shorter time to vessel occlusion (4.9±0.3 min [1-11 mPC]-mFVIIa vs. 12.9±1.4 min [mFVIIa]). Flow/min vs. time for this experiment is shown in FIG. 9B. Administration of [1-11 mPC]-mFVIIa at 1 mg/kg resulted in vessel occlusion in 33% of mice in contrast to mFVIIa where no vessel occlusion was observed. The data shown in Table 1 demonstrate that allowing mFVIIa to bind murine EPCR (i.e. variant [1-11 mPC]-mFVIIa) results in enhanced hemostatic function, therefore EPCR appears to play a positive role in FVIIa-induced hemostasis in this animal model. Since human FVIIa interacts with human EPCR, it is expected that, following its administration in hemophilia treatment, a proportion of the FVIIa hemostatic function may be through its interaction with EPCR on the damaged vessel(s). As a result, part of this invention concerns the design of variants of FVII with enhanced EPCR binding capacity (and hemostatic properties) for treatment of coagulation defects or even off-label applications (where >90% of FVIIa usage lies).

this human FVIIa DNA sequence, we generated all possible amino acid variants at position 8 in human FVIIa, normally occupied by a Leu amino acid. For each construct, we used transient DNA transfection in human embryonic kidney cells (HEK-293) in the presence of vitamin K. Forty-eight hours after transfection, we collected culture medium and determined the clotting activity and human FVIIa antigen levels in the culture medium using a clotting assay and an enzyme-linked immunosorbent assay (ELISA), respectively. Specific activity was defined as the ratio of clotting activity/antigen, using the wildtype construct (Leu [L]) as 100%. In data shown in FIG. 11, it is evident that some modifications at position 8 result in proteins with no detectable specific activity (Asn [N], Asp [D], Lys [K], Cys [C] and Glu [E]). On CHO-K1 cells expressing human EPCR, we added culture medium containing human FVIIa variants at position 8 that retain activity (shown in FIG. 11). We determined whether changes in the amino acid at this position affect binding of human FVIIa to human EPCR. FIG. 12 shows that the only modification that allows for binding to human EPCR (apart from the wild type amino acid [Leu]), is isoleucine (I). Therefore, we have indentified human FVIIa variants with a change in position 8 (as shown in FIG. 12) that result in lack of human EPCR binding but retain clotting activity. Such molecules are expected to have increased circulatory half-lives, since FVIIa binding to EPCR sequesters FVIIa from the circulation (an example is shown in FIG. 5B). Therefore, use of molecules with reduced EPCR binding but increased circulatory half-lives should result in an improved net hemostatic outcome, compared to the FVIIa molecule used clinically today. However, in the context of the Gla domain of human FVIIa, other modifications, that may include combination of amino acid changes at Phe4

TABLE 1

Data from FeC13 model of arterial thrombosis. Type of mice and number of mice (N) is shown, along with the protein and dose received following a 10 min observation period after FeCl3 injury (as described in FIG. 9B). Vessel occlusion is categorized as none, transient or complete. The number of mice exhibiting each type of occlusion is indicated. Number of mice with full occlusion are shown, as well as a percentage of total mice infused with each protein and dose. Time to vessel occlusion is indicated.

| Sample | Dose of protein infused (mg/kg) | N | No occlusion | Transient occlusion | Complete occlusion (N) | Time to occlusion (min) |
|---|---|---|---|---|---|---|
| Hemophilia B + | 5 | 3 | — | — | 3 (100%) | 4.30.6 |
| mFVIIa | 3 | 4 | 1 | — | 3 (75%) | 12.9 ± 1.4 |
| Hemophilia B + (1- | 5 | 3 | — | — | 3 (100%) | 2.6 ± 0.4 |
| 11 mPC)-mFVIIa | 3 | 5 | — | — | 5 (100%) | 4.9 ± 0.3 |
| | 1 | 3 | 2 | — | 1 (33%) | 6.0 |
| Hemophilia A + mFVIIa | 3 | 4 | — | — | 4 (100%) | 13.8 ± 0.8 |
| Hemophilia A + (1-11 mPC)-mFVIIa | 3 | 5 | — | — | 5 (100%) | 2.8 ± 0.3 |
| Normal C57BL/6 | — | 5 | — | — | 5 (100%) | 14.5 ± 0.3 |

In human protein C, amino acids at position 4 and 8 are primarily implicated in human PC-human EPCR interaction. Human FVIIa shares identity with human protein C at these positions therefore modification at these locations will generate human FVII polypeptides with modified EPCR binding capacities. However, modification may also affect the specific activity of the resulting molecule. We have previously described a transgene coding for activated human FVII (using a PACE/furin cleavage site) (Margaritis P et al., J Clin Invest 2004). Using an expression plasmid containing (also shown in FIG. 6) and Leu8, that alter (enhance or reduce) the FVIIa-EPCR interaction should also result in detectable specific activity. Similar changes in human FVII (shown in FIG. 13) should also result in a net hemostatic beneficially therapeutic outcome. Ultimately, a desirable human FVII polypeptide will combine the EPCR binding capacity and specific activity that provide it with superior hemostatic properties in vivo.

Data from rFVIIa prophylaxis demonstrate clinical benefits (e.g. number of bleeds) continuing well beyond the end of prophylaxis, suggestive of an extended persistence of rFVIIa in patients outside the vascular bed. Furthermore, previous mouse studies have shown that (1) tissue factor and FVIIa colocalize in the perivascular space (Hoffman M et al., J Thromb Haemost 2007); and (2) EPCR is involved in the transfer of infused rFVIIa across the vascular bed (Clark C A et al., J Thromb Haemost 2012). Taken together, it is possible that the long-term clinical benefits seen with rFVIIa prophylaxis may also be attributed indirectly to an EPCR-dependent perivascular FVIIa transfer and localization. There, complexed with TF, it can potentially prevent bleeds in the microcirculation before they escalate to full bleeds. As such, the data provided herein also suggest that changes in human FVII to allow for tighter binding to EPCR should offer an additional advantage to resulting FVII polypeptides in a setting of prophylaxis either by protein administration or by continuous or regulated expression following genetic transfer of transgenes encoding such FVII polypeptides. In the same setting, changes in human FVII that can affect its circulatory half-life should also be clinically beneficial. Such molecules (example of which are shown in FIG. 12 [for human activated FVII] and FIG. 13 [for human FVII]) should provide reduced EPCR binding but overall enhanced hemostatic capacity (compared to standard or wild-type FVII and activated FVII) due to their increased circulatory half-life. In essence, increased circulatory half-life should compensate for the reduced EPCR binding, resulting in a net improvement in hemostatic capacity. Thus, this invention encompasses variants of FVII which exhibit altered EPCR interactions and thereby provide improved net hemostatic outcome.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An isolated human Factor VII (FVII) variant having 1 to 2 amino acid substitutions in its Gla domain, wherein the Gla domain comprises SEQ ID NO: 10, wherein the amino acid substitutions are selected from the group consisting of i) a substitution of Phenylalanine at position 4 in of SEQ ID NO: 10 with an amino acid selected from Tryptophan, Glycine, Glutamic acid, Aspartic acid, Valine, Lysine, Serine, Tyrosine, Cysteine, Histidine, Glutamine, Arginine, Methionine, Isoleucine, Threonine, and Asparagine and, or, ii) a substitution of Leucine at position 8 of the of SEQ ID NO: 10 with an amino acid selected from Alanine, Tryptophan, Glycine, Phenylalanine, Serine, Tyrosine, Proline, Histidine, Glutamine, Arginine, Methionine, Isoleucine, Threonine, and Valine;

wherein if said Leucine at position 8 is substituted with Alanine, then position 4 is substituted with an amino acid listed in (i) and wherein said variant exhibits hemostatic effects via altered endothelial protein C receptor (EPCR) binding relative to FVII or FVIIa lacking said amino acid substitutions.

2. The variant of claim 1, wherein said variant is recombinantly produced.

3. The variant of claim 1, wherein said substitution at position 8 is selected from Alanine, Methionine, Phenylalanine, Tryptophan, Threonine, Tyrosine, and Valine, said variant having an increased circulatory half-life.

4. A nucleic acid encoding the variant of claim 2.

5. A pharmaceutical composition comprising the variant of claim 1 in a biologically compatible carrier suitable for use in humans.

6. The nucleic acid of claim 4 cloned into an expression vector.

7. The vector of claim 6, selected from the group consisting of an adenoviral vector, an adenovirus-associated vector, a retroviral vector, a plasmid, and a lentiviral vector.

8. A method for treatment of a hemostasis related disorder in a patient in need thereof comprising administering a therapeutically effective amount of the variant FVII of claim 1 or 2 in a biologically acceptable carrier.

9. The method of claim 8, wherein said variant is activated FVII variant.

10. The method of claim 8, wherein said variant is a pro-coagulant and said disorder is selected from the group consisting of hemophilia A, hemophilia B, FVII deficiency, Glanzmann's thrombasthenia, Bernard-Soulier syndrome, von Willebrand diseases, bleeding associated with trauma, injury, thrombosis, thrombocytopenia, stroke, coagulopathy, disseminated intravascular coagulation (DIC) and over-anticoagulation treatment disorders.

11. The method of claim 8, wherein said variant is encapsulated in a liposome or mixed with phospholipids or micelles.

12. An isolated host cell expressing the variant of claim 2.

13. The variant of claim 2 in a pharmaceutical composition suitable for use in humans.

14. The variant of claim 3 in a pharmaceutical composition suitable for use in humans.

15. The variant of claim 1, wherein said substitution at position 8 is isoleucine, said variant retaining clotting activity and ability to bind EPCR.

* * * * *

SEQUENCE LISTING

<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: mF7a

<400> SEQUENCE: 1

Ala Asn Ser Leu Leu Glu Glu Leu Trp Pro Gly Ser Leu Glu Arg Glu
1 5 10 15

Cys Asn Glu Glu
20

<210> SEQ ID NO 2
<211> LENGTH: 20
<212> TYPE: PRT
<213> ORGANISM: Artificial Sequence
<220> FEATURE:
<223> OTHER INFORMATION: (1-11mPC)-mF7a

<400> SEQUENCE: 2

Ala Asn Ser Phe Leu Glu Glu Met Arg Pro Gly Ser Leu Glu Arg Glu
1 5 10 15

Cys Asn Glu Glu
20

<210> SEQ ID NO 3
<211> LENGTH: 20
<212> TYPE: PRT
<213> ORGANISM: Artificial Sequence
<220> FEATURE:
<223> OTHER INFORMATION: mF7a L4F

<400> SEQUENCE: 3

Ala Asn Ser Phe Leu Glu Glu Leu Trp Pro Gly Ser Leu Glu Arg Glu
1 5 10 15

Cys Asn Glu Glu
20

<210> SEQ ID NO 4
<211> LENGTH: 20
<212> TYPE: PRT
<213> ORGANISM: Artificial Sequence
<220> FEATURE:
<223> OTHER INFORMATION: mF7a L8M

<400> SEQUENCE: 4

Ala Asn Ser Leu Leu Glu Glu Met Trp Pro Gly Ser Leu Glu Arg Glu
1 5 10 15

Cys Asn Glu Glu
20

<210> SEQ ID NO 5
<211> LENGTH: 20
<212> TYPE: PRT
<213> ORGANISM: Artificial Sequence
<220> FEATURE:
<223> OTHER INFORMATION: mF7a W9R

<400> SEQUENCE: 5

Ala Asn Ser Leu Leu Glu Glu Leu Trp Pro Gly Ser Leu Glu Arg Glu
1 5 10 15

Cys Asn Glu Glu
20

<210> SEQ ID NO 6
<211> LENGTH: 20
<212> TYPE: PRT
<213> ORGANISM: Artificial Sequence
<220> FEATURE:
<223> OTHER INFORMATION: mPC

<400> SEQUENCE: 6

Ala Asn Ser Phe Leu Glu Glu Met Arg Pro Gly Ser Leu Glu Arg Glu
1 5 10 15

Cys Met Glu Glu
20

<210> SEQ ID NO 7
<211> LENGTH: 20
<212> TYPE: PRT
<213> ORGANISM: Artificial Sequence
<220> FEATURE:
<223> OTHER INFORMATION: mPC F4L

<400> SEQUENCE: 7

Ala Asn Ser Leu Leu Glu Glu Met Arg Pro Gly Ser Leu Glu Arg Glu
1 5 10 15

Cys Met Glu Glu
20

<210> SEQ ID NO 8
<211> LENGTH: 20
<212> TYPE: PRT
<213> ORGANISM: Artificial Sequence
<220> FEATURE:
<223> OTHER INFORMATION: mPC M8L

<400> SEQUENCE: 8

Ala Asn Ser Phe Leu Glu Glu Leu Arg Pro Gly Ser Leu Glu Arg Glu
1 5 10 15

Cys Met Glu Glu
20

<210> SEQ ID NO 9
<211> LENGTH: 20
<212> TYPE: PRT

-continued

```
<213> ORGANISM: Artificial Sequence
<220> FEATURE:
<223> OTHER INFORMATION: mPC R9W

<400> SEQUENCE: 9

Ala Asn Ser Phe Leu Glu Glu Met Trp Pro Gly Ser Leu Glu Arg Glu
 1              5                   10                  15

Cys Met Glu Glu
            20


<210> SEQ ID NO 10
<211> LENGTH: 10
<212> TYPE: PRT
<213> ORGANISM: Artificial Sequence
<220> FEATURE:
<223> OTHER INFORMATION: human FVIIa fragment

<400> SEQUENCE: 10

Ala Asn Ala Phe Leu Glu Glu Leu Arg Pro
 1              5                   10


<210> SEQ ID NO 11
<211> LENGTH: 6
<212> TYPE: PRT
<213> ORGANISM: Artificial Sequence
<220> FEATURE:
<223> OTHER INFORMATION: human FVIIa fragment

<400> SEQUENCE: 11

Arg Lys Arg Arg Lys Arg
 1              5
```